(12) United States Patent
Danforth, Jr. et al.

(10) Patent No.: US 6,740,680 B1
(45) Date of Patent: May 25, 2004

(54) PHARMACEUTICAL COMPOSITIONS TO TETRAC AND METHODS OF USE THEREOF

(75) Inventors: Elliot Danforth, Jr., Underhill, VT (US); Albert Burger, Geneva (CH)

(73) Assignee: Becton Pharma, Inc., Underhill, VT (US)

( * ) Notice: Subject to any disclaimer, the term of this patent is extended or adjusted under 35 U.S.C. 154(b) by 0 days.

(21) Appl. No.: 10/019,623

(22) PCT Filed: Apr. 25, 2000

(86) PCT No.: PCT/US00/11166
§ 371 (c)(1),
(2), (4) Date: May 9, 2002

(87) PCT Pub. No.: WO00/64431
PCT Pub. Date: Nov. 2, 2000

Related U.S. Application Data (60) Provisional application No. 60/130,961, filed on Apr. 26, 1999.

(51) Int. Cl.[7] .............................................. A61K 31/19
(52) U.S. Cl. ....................................................... 514/570
(58) Field of Search ......................................... 514/570

(56) References Cited

U.S. PATENT DOCUMENTS

| | | | | |
|---|---|---|---|---|
| 4,741,897 A | * | 5/1988 | Andrews et al. | 436/500 |
| 5,714,142 A | * | 2/1998 | Blaney et al. | 424/85.2 |
| 5,736,576 A | * | 4/1998 | Kun et al. | 514/568 |

FOREIGN PATENT DOCUMENTS

| | | | |
|---|---|---|---|
| WO | 96/40048 | * 12/2002 | 514/570 |

OTHER PUBLICATIONS

Everts et al; Department of Internal Medicine, Erasmus University Medical School, Rotterdam, The Netherlands, "Uptake of 3,3'5,5'–Tetraiodothyroacetic Acid and 3,3', 5'–Triiodothyronine in Cultured Rat Anterior Pituitary Cells and Their Effects on Thyrotropin Secretion". Endocrinology 1995;135(10): pp. 4454–4461.

Burger et al; "The Effects of Tetraiodothyroacetic and Triiodothyroactic Acids on Thyroid Function in Euthyroid and Hyperthyroid Subjects". Acta Endocrinologica 1979; (92)455–467.

* cited by examiner

Primary Examiner—James H Reamer
(74) Attorney, Agent, or Firm—Edwards & Angell, LLP; David G. Conlin (57) ABSTRACT

The present invention provides novel pharmaceutical compositions and methods of treatment that utilize or comprise tetrac and/or another thyromimetic compound. The pharmaceutical compositions of the invention are capable of suppressing TSH secretion without inhibiting the pituitary specific monodeiodinase type II and while reducing or avoiding the thyromimetic stimulation of peripheral tissues compared to equivalent TSH-suppressive doses of L-thyroxine (T4). The pharmaceutical compositions of the invention are particularly useful for treating patients suffering from malignancy or abnormal growth of the thyroid and for preventing growth of residual thyroid tissue post thyroidectomy.

7 Claims, 7 Drawing Sheets

PHARMACEUTICAL COMPOSITIONS TO TETRAC AND METHODS OF USE THEREOF

This application claims the benefit of U.S. Provisional Application No. 60/130,961, filed Apr. 26, 1999, which is incorporated herein by reference.

BACKGROUND OF THE INVENTION

1. Field of the Invention

The present invention relates to novel pharmaceutical compositions and methods of treatment that utilize or comprise tetrac (3,3',5,5'-tetraiodothyroacetic acid), a natural metabolite of the thyroid hormone T4 (L-thyroxine). Pharmaceutical compositions of the invention are capable of suppressing the secretion of thyroid stimulating hormone (TSH) while reducing or avoiding the thyromimetic stimulation of peripheral tissues as compared to an equivalent TSH-suppressive dose of L-thyroxine.

2. Background

The thyroid is a bilobal gland located at the base of the neck in front of the windpipe. It produces a variety of hormones that regulate body metabolism and organ function and thus affects such things as heart rate, cholesterol level, body weight, energy level, muscle strength and skin condition, among other things. The thyroid hormones bind to protein receptors closely associated with DNA in the nucleus of the cells of the body thereby regulating the transcription of DNA and the translation of RNA. Therefore, the metabolic effects of the thyroid hormones derive from their ability to regulate the turnover of enzymes and proteins in the body.

Figure 1:
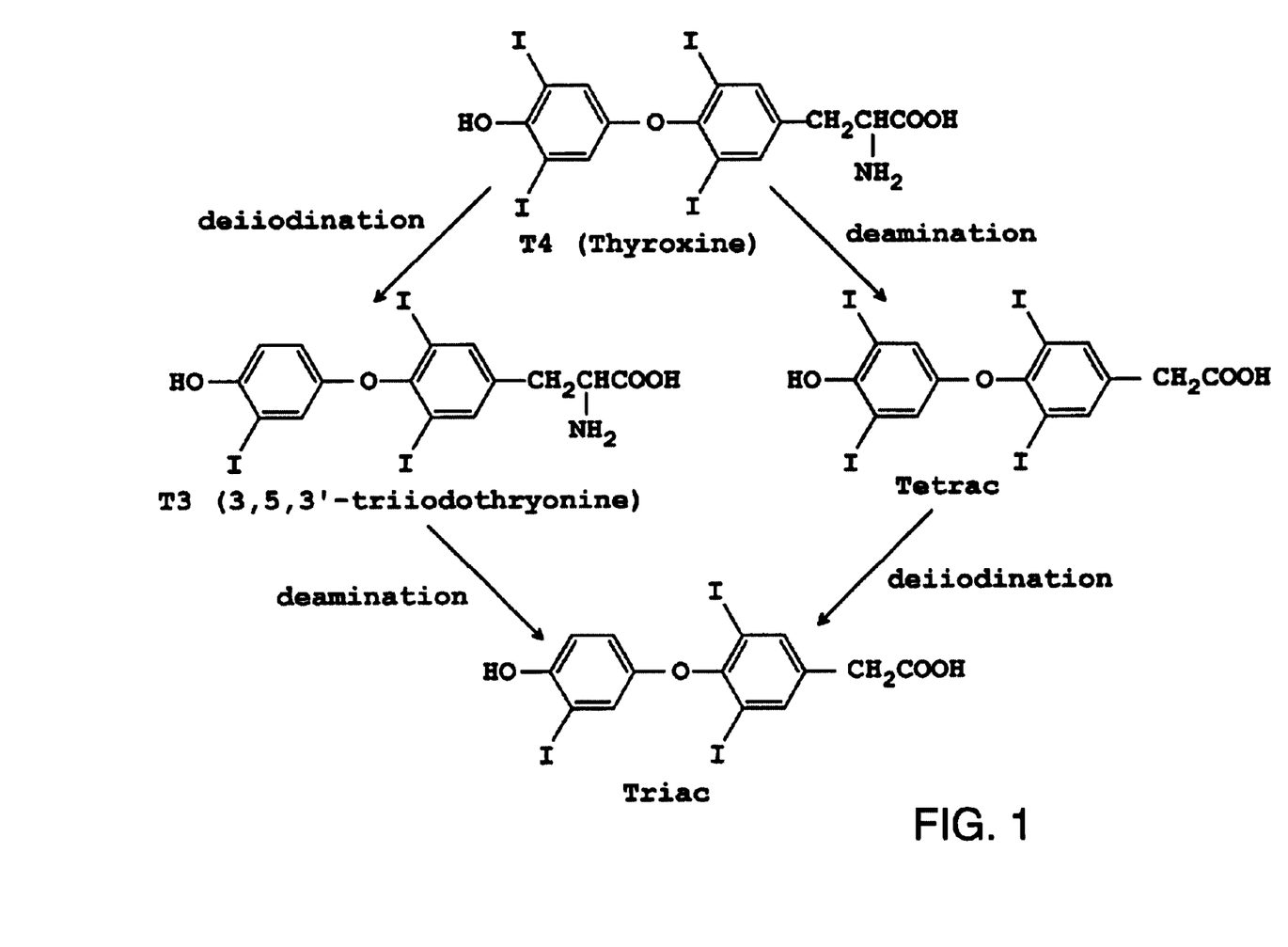
FIG. 1 shows the structures of T4 (L-thyroxine), T3 (3,5,3'-triidodothyronine), tetrac (3,3',5,5'-tetraiodothyroacetic acid) and triac (3,3',5-triiodothyroacetic acid).

The amount of thyroid hormone present in the body is carefully regulated by a feedback mechanism involving the hypothalamus, pituitary and thyroid glands. The hypothalamus produces thyrotropin releasing hormone (TRH) which causes the pituitary to produce thyroid stimulating hormone (TSH). TSH stimulates the thyroid to produce T4 (thyroxine) and T3 (3,3',5-triiodothyronine), the two major thyroid hormones (FIG. 1). The levels of T4 and T3 in the blood are monitored by the pituitary which will produce more TSH if the thyroid hormone levels are too low and less TSH if the levels of T3 and T4 are too high.

T4 is the principal secretory product of the thyroid gland while T3 is the most potent thyroid hormone due to its high binding affinity for the thyroid hormone nuclear receptors. Secretion of TSH from the pituitary gland is exquisitely sensitive to inhibition by T3. Although T3 is only secreted by the thyroid gland in small amounts, its principle source in the pituitary gland is through the local conversion of T4 to T3 by the pituitary specific enzyme, monodeiodinase type II. The control of pituitary TSH secretion therefor depends on the activity of this monodeiodinase. As the circulating concentrations of T4 approach normal levels, T4 suppresses the activity of the pituitary specific monodeiodinase type II thus reducing T3 generation and effectively releasing the pituitary from further suppression. The ability of T4 to control the suppression of TSH secretion accounts for the feedback regulation of T4 on its own secretion and the normal set-point of the thyroid-pituitary axis.

The presence of too much or too little thyroid hormone in the body leads to abnormalities which can become life-threatening if left untreated. The presence of too much thyroid hormone leads to hyperthyroidism. Hyperthyroidism, or overactivity of the thyroid gland, has several causes and amongst other symptoms causes anxiety, insomnia, weight loss and rapid heart rate. Hyperthyroidism is treated by destruction of all or part of the thyroid gland by surgical removal, treatment with radioiodine, or both, and with drugs that block the synthesis of the thyroid hormones.

The presence of too little thyroid hormone leads to hypothyroidism which is more common than hyperthyroidism. Hypothyroidism, or underactivity of the thyroid gland, has several causes and amongst other symptoms causes lassitude, weakness, weight gain and slow heart rate. Hyperthyroidism is treated by lifelong replacement with synthetic thyroid hormones, usually L-thyroxine.

Abnormal growths or cancers of the thyroid gland are presently treated by surgical removal of the gland followed by radioiodine to destroy any remaining thyroid tissue. This is followed by chronic treatment with supraphysiologic doses of T4 to suppress the secretion of TSH from the pituitary gland, thereby preventing stimulation of residual thyroid cancer cells expressing the TSH receptor. These supraphysiologic suppressive doses of T4 unavoidably lead to mild hyperthyroidism.

Other metabolites of the thyroid hormones are tetrac (3,3',5,5'-tetraiodothyroacetic acid) and triac (3,3',5-triiodothyroacetic acid) which are produced by the deamination of T4 and T3, respectively (FIG. 1). Tetrac is a prohormone of triac and is converted by two enzymes, the same monodeiodinase type II found in the pituitary and to some extent elsewhere in the brain and at low expression in the heart and thyroid gland and monodeiodinase type I found in the liver and other peripheral tissues that converts T4 to T3. Triac is also a potent inhibitor of TSH secretion and has been investigated as a substitute for T4 in treating thyroid patients after thyroidectomy. However, because of its potent thyromimetic activity in peripheral tissues and very short plasma half-life, triac was found to be an unsuitable substitute for T4 for this purpose. However, triac has been found to be useful in treating a rare form of thyroid hormone resistance.

Thus, it would be extremely desirable to develop novel pharmaceutical compositions capable of suppressing TSH secretion while reducing or avoiding the iatrogenic hyperthyroidism induced by comparable TSH-suppressive doses of T4 (L-thyroxine).

See also: Bracco, D., et al. *J. Clin. Endocrinol. Metab.*, 77: 221–228 (1993); Burger, A. G. and Vallotton, M. B., "The metabolism of tetraiodothyroacetic acid and its conversion to triiodothryoacetic acid," *Thyroid Hormone Metabolism*, pages 223–239, W. A. Harland and J. S. Orr, editors, Academic Press, London, New York, San Francisco, (1975); Burger, A. G. et al. *Acta Endocrinologica*, 92: 455–467 (1979); Goolden, A. W. G., et al. *The Lancet*, 1: 890–891 (1956); Green, W. L. and Ingbar, S. H. *J. Clin Endocr.*, 21: 1548–1565 (1961); Lerman, J. and Pitt-Rivers, R. *J. Clin. Endocrinol. Metab.*, 16: 1470–1479 (1956); Lerman, J., *J. Clin. Endocr.*, 21: 1044–1053 (1961); Liang, H., et al. *Eur. J. Endocrinol.*, 137: 537–544 (1997); Menegay, C., et al. *Acta Endocrinol. (Copenh)*, 121: 651–658 (1989); and Richardson-Hill, S., et al. *J. Clin. Invest.*, 39: 523–533 (1960).

SUMMARY OF THE INVENTION

The present invention provides novel pharmaceutical compositions comprising tetrac which are capable of suppressing TSH secretion while reducing or avoiding the thyromimetic stimulation of peripheral tissues induced by a dose of L-thyroxine which produces an equivalent TSH-suppressive effect. The invention further provides pharmaceutical composites that comprise a combination of tetrac and L-thyroxine (T4).

Preferred pharmaceutical compositions are capable of suppressing TSH secretion while reducing or avoiding the thyromimetic stimulation of the tissues of the heart, liver, kidneys, muscle and bone as compared to the stimulation of said tissues induced by a dose of L-thyroxine which produces an equivalent TSH-suppressive effect.

The compositions of the present invention are capable of suppressing TSH secretion without suppressing the activity of the pituitary specific type II monodeiodinase.

The invention provides a method for suppressing TSH secretion while reducing or avoiding the thyromimetic stimulation of peripheral tissues induced by a dose of L-thyroxine which produces an equivalent TSH-suppressive effect comprising administration of a pharmaceutical composition comprising tetrac.

The method of the present invention may be used to treat patients suffering from malignancies or other abnormal growths of the thyroid gland. The method of the present invention is particularly useful for suppressing the growth of residual thyroid tissue in a thyroid cancer patient post thyroidectomy.

Tetrac is a natural metabolite of thyroxine (T4), the main secreted thyroid hormone. The thyromimetic potency of tetrac is less than triac because of its lower binding affinity for the thyroid hormone nuclear receptors. Additionally, tetrac is locally converted to triac, a potent inhibitor of TSH secretion, by the pituitary specific type II monodeiodinase. Due to its long half-life, tetrac assures a constant supply of triac and the small amounts of locally produced triac in the pituitary and its rapid metabolic half-life limits the thyromimetic activity of triac in other tissues of the body. Moreover, tetrac, unlike T4, does not suppress the activity of the pituitary specific monodeiodinase as its concentration in the plasma is increased. Therefore, following conversion to triac, tetrac is capable of suppressing TSH in an unrestrained fashion. In addition, tetrac is less thyromimetic in peripheral tissues as compared to T4 and is pharmaceutically more elegant than triac because of its longer plasma half-life.

Other aspects of the invention are disclosed infra.

BRIEF DESCRIPTION OF THE DRAWINGS

FIG. 2 shows the effects of T4 and tetrac treatment on cardiac monodeiodinase type I activity (panel a) and SERCA mRNA levels (panel b) in treated rats.

FIG. 3 shows the effects of T4 and tetrac treatment on α- and β-MHC mRNA levels (panels a and b, respectively) in treated rats.

FIG. 4 shows the effects of T4 and tetrac treatment on hepatic monodeiodinase type I activity (panel a) and hepatic monodeiodinase type I mRNA levels (panel b) in treated rats.

FIG. 5 shows the effects of T4 and tetrac treatment on growth hormone (GH) mRNA levels (panel a) and monodeiodinase type II mRNA levels (panel b) in treated rats.

FIG. 6 shows the effects of T4 and tetrac treatment on monodeiodinase type II activity in brain cortex (panel a) and brown adipose tissue (BAT) (panel b) in treated rats.

DETAILED DESCRIPTION OF THE INVENTION

We have now discovered that pharmaceutical compositions comprising tetrac are useful as thyromimetic drugs for the treatment of mammals, particularly humans, suffering from iatrogenic hypothyroidism. More particularly, compositions of the invention are capable of suppressing the secretion of TSH while reducing or abolishing the iatrogenic hyperthyroidism induced by equivalent TSH-suppressive doses of L-thyroxine. Compounds of the invention are particularly useful for treating thyroid cancer patients post thyroidectomy because they are able to completely or almost completely suppress the secretion of TSH and thereby prevent stimulation of the growth of residual thyroid tissue. Compositions of the invention may also comprise other thyromimetic compounds, particularly L-thyroxine.

Pharmaceutical compositions of the invention will be useful in treating mammals, particularly humans, suffering from iatrogenic hypothyroidism. Specific examples of iatrogenic hypothyroidism are partial or complete destruction of the thyroid by radioiodide treatment, partial or complete surgical removal of the thyroid or drug inhibition of thyroid hormone production. Compositions of the invention are particularly useful for treating patients with abnormal or malignant growths of the thyroid, including well-differentiated thyroid cancers such as papillary, follicular and combined papillary/follicular cancers. Preferably compositions of the invention are administered to patients post thyroidectomy to relieve symptoms of hypothyroidism and to prevent stimulation and regrowth of residual thyroid tissues.

The invention also provides methods for administering pharmaceutical compositions comprising tetrac or tetrac in combination with other thyromimetic compounds to suppress TSH secretion in a mammal. Preferred thyromimetic compounds useful for compositions of the invention include T4, T3 and triac. Pharmaceutical compositions comprising tetrac and T4 are particularly preferred.

Administration of compounds of the invention may be made by a variety of suitable routes including oral, topical (including transdermal, buccal or sublingal), nasal and parenteral (including intraperitoneal, subcutaneous, intravenous, intradermal or intramuscular injection) or other suitable forms. It will be appreciated that the actual preferred amounts of active compounds in a given therapy will vary according to the specific compound being utilized, the particular compositions formulated, the mode of application, the particular site of administration, the condition and age of the recipient, etc. Optimal administration rates for a given protocol of administration can be readily ascertained by those skilled in the art using conventional dosage determination tests.

Dosages of thyromimetic compounds may be generally in the range of 0.01 to 10,000 μg/kg body weight. Preferred dosages of tetrac are 0.1 to 1,000 μg/kg, particularly preferred dosages or tetrac are 1 to 200 μg/kg.

Compositions of the invention comprising tetrac or tetrac in combination with another thyromimetic compound, may be administered alone, they also may be present as part of a pharmaceutical composition in a mixture with a pharmaceutically acceptable organic or inorganic carrier substance suitable for parenteral, oral or other desired route of administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, glucose, mannose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, cyclodextrans, fish oils; components of fish oils, triglycerides, ω-3-fatty acids, ω-3-fatty acid esters, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds. These compositions can also be freeze-dried and reconstituted in appropriate solvents.

For parenteral application, particularly suitable are solutions, preferably oily or aqueous slightly alkaline solutions, carrier proteins as well as suspensions, emulsions or implants, including suppositories. Ampules are convenient for administration of unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differently degradable coatings, e.g., by microencapsulation, multiple coatings, etc.

Therapeutic compounds of the invention also may be incorporated into liposomes. The incorporation can be carried out according to known liposome preparation procedures, e.g. sonication and extrusion. Suitable conventional methods of liposome preparation are also disclosed in e.g. A. D. Bangham et al., *J. Mol. Biol.*, 23:238–252 (1965); F. Olson et al., *Biochim Biophys. Acta*, 557:9–23 (1979); F. Szoka et al., *Proc. Nat. Acad. Sci.*, 75:4194–4198 (1978); S. Kim et al., *Biochim. Biophys. Acta*, 728:339–348 (1983); and Mayer et al., *Biochim. Biophys. Acta*, 858:161–168 (1986).

The liposome may be made from any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine or phosphatidylinositol. Synthetic phospholipids may also be used e.g., dimyristoylphosphatidylcholine, dioleoylphosphatidycholine and corresponding synthetic phosphatidylethanolamines and phosphatidylglycerols. Cholesterol or other sterols, cholesterol hemisuccinate, glycolipids, 1,2-bis(oleoyloxy)-3-(trimethyl ammonio)propane (DOTAP), N-[1-(2,3-dioleoyl)propyl]-N,N,N-trimethylammonium choloride (DOTMA), and other cationic lipids may be incorporated into the liposomes. The relative amounts of tetrac and other thyromimetic compounds and additives used in the liposomes may vary relatively widely. Liposomes of the invention suitably contain about 60 to 90 mole percent of natural or synthetic phospholipid; cholesterol, cholesterol hemisuccinate, fatty acids or cationic lipids may be used in amounts ranging from 0 to 50 mole percent; and the one or more therapeutic compounds of the invention may be suitably present in amounts of from about 0.01 to about 50 mole percent.

The present invention is further illustrated by the following examples. These examples are provided to aid in the understanding of the invention and are not to be construed as limitations thereof.

EXAMPLE 1

Preparation of 3,3',5,5'-Tetraiodothyroacetic Acid (Tetrac)

Synthesis procedures for production of the thyroid hormones is well known in the art (see, e.g. Stewart C. Harvey et al., *Remington's Pharmaceutical Sciences*, 18$^{th}$ ed., Mack Publishing Co., Easton, Pa., U.S.A., pages 979–981).

In general, tetrac may be obtained by iodination of triac or 4'-hydroxy 3,3',5-triiodophenoxy phenyl acetate by mixing a mixture of iodine and iodide in an aqueous solution. The purification of tetrac from triac is obtained by several crystallizations in acetone.

Tetrac is commercially available from a number of companies including Firma Formula GmbH (Berlin, Germany), Simafex (Marans, France), ICMD (Mulhouse-Dornach, France) and Sigma (St. Louis, Mo.).

EXAMPLE 2

Effects of Tetrac on TSH Suppression and Cardiac Parameters in the Rat

Thyroid hormones (3,3'-T2, T3, T4) and their analogs Diac, Triac and Tetrac were obtained from Henning Co. (Berlin, Germany). All the chemical reagents used were purchased from Fluka (Buchs, Switzerland), from Sigma Chemical Co. (St-Louis, USA) or Merck (Darmstadt, Germany). Osmotic mini-pumps (model 2002) were purchased from Alzet (Palo Alto, USA). Carrier-free [$^{125}$I]Na was purchased from Amersham International (Buckinghamshire, UK) and [$^{131}$I]Na from the Nuklear Reaktor, Wurenlingen, Switzerland. T3, T4, Triac and Tetrac were labeled with $^{125}$I by the chloramine-T method using 3,5-T2, L-T3, Diac and Triac as substrate respectively (Burger, A. et al. Endocrinology (1975) 97: 919–923). Specific activities thus achieved were higher than 1200 µCi/µg.

Seventy-nine male SIVZ rats were purchased from the breeder (Institut für Labortierkunde des Universität Zürich, Zürich, Switzerland). They were rendered hypothyroid by a single injection of [$^{131}$I]Na (100 µCi/rat) and before and throughout the experiment 0.02% 2-mercapto-1-methylimidazol (MMI) was added to drinking water. In order to have an euthyroid control group of similar weight and identical age, 10 rats received only MMI in the drinking water and 2 weeks before implanting the minipumps, MMI was withdrawn. Osmotic minipumps (secretion rate 0.25 µl/hour, duration 14 days) were implanted intraperitoneally (i.p.) 2 months after the injection of [$^{131}$I]Na. The minipumps were filled with T4 or Tetrac dissolved in 0.05 N NaOH, 2% BSA and 100,000 cpm [$^{125}$I]T4 or [$^{125}$I]Tetrac as control of their secretion rates. The infusion lasted 13 days. 0, 1.5, 4.5, 13.5 and 40.5 nmol Tetrac/day/100 g or 0.5, 1.5, 4.5 and 13.5 nmol T4/day/100 g bodyweight (BW) (n=4/dose) were infused. An euthyroid control group was included. The animals were weighed every 2 days. Rats were sacrificed by decapitation and blood was collected and stored at −200° C. until use. Tissues (liver, heart, brown adipose tissue, cerebral cortex and pituitary) were removed rapidly, frozen in liquid nitrogen and stored at −700° C. until use.

Hornone assays. Total serum T4, T3, Tetrac, Triac and TSH levels (intra-assay coefficient of variation 7 to 10%, inter-assay coefficient of variation 12 to 15%) were measured using the method of Burger, A., Sakoloff, C., Staeheli, V., Vallotton, M. D., and Ingbar, S. H. Acta. Endocrinol. (Copenh.) 80: 58–69 (1975). Serum TSH measurements were performed with reagents kindly provided by the National Pituitary Program, NIAMDD, NIH (Bethesda, USA). The detection limits were 0.80 ng TSH/ml; 9.5 pmol T4/ml; 0.16 pmol T3/ml; 10 pmol Tetrac/ml and 0.52 pmol Triac/ml.

Monodeiodinase type 1 and 2 activities. Monodeiodinase type 1 and type 2 activities were determined in tissue homogenates by measuring the release of radioiodide from [$^{125}$I]rT3 according to the method of Leonard and Rosenberg (Leonard, J. L. et al. Endocrinology (1980) 106: 444–451).

Monodeiodinase type 1 activity was measured in liver homogenates using 1 $\mu$M rT3 and 1 mM DTT with 10 min of incubation, whereas for heart, 0.01 $\mu$M rT3 and 10 mM DTT with 1 hour of incubation. Monodeiodinase type 2 activity was measured in brown adipose tissue (BAT) and cerebral cortex using 1 nM rT3, 10 mM DTT and 1 mM propylthiouracil (PTU) with 1 hour of incubation. Protein concentrations were measured by the method of Bradford (Bio-Rad Laboratories GmbH, Munich, Germany) with bovine gammaglobulin as the protein standard. In order to study the effect of circulating Tetrac on the enzyme activities, 2 rats were injected intraperitoneally with 10 $\mu$Ci $^{125}$I Tetrac and killed 6 hours later. The tissue homogenates were extracted with 3 volumes of ethanol-NH3 (97:3). After 10 minutes centrifugation at 15,000 g, the supernatant was vacuum dried and applied to TLC (Merck 254, Toluol, acetic acid, water: 2:2:1). In order to calculate the tissue concentrations, the highest serum Tetrac levels were used (406 pmol/ml). The calculated tissue concentrations were: liver: 1.9, heart: 2.29 and brain cortex: 0.47 fluol Tetrac/$\mu$g protein.

Total RNA extraction and Northern Blot hybridization Total RNA was extracted with the method of Chomczynski and Sacchi (Chomczynski, P. and Sacchi, N. Anal. Biochem. (1987) 162: 156–159). The probe for monodeiodinase type 1 was kindly provided by Dr. P. R. Larsen (Harvard Medical School, Boston, USA); for monodeiodinase type 2 by Dr. D L St. Gerrnain, Lebanon, N H, the rat growth hormone probe (rGH) by Dr. F. DeNoto (University of California, San Francisco, USA); and the probe for rat cardiac reticulum sarcoplasmic $Ca^{2+}$-ATPase (SERCA2) by Dr. W. H. Dillmann and Dr. R. Sayen (Medical Center of University of California, San Diego, USA). The probes for $\alpha$- and, $\beta$-myosin heavy chain ($\alpha$-MHC and $\beta$-MHC) were synthesized by Microsynth (Microsynth GmbH, Balgach, Switzerland). Probes were labeled by $\gamma[^{32}P]dCTP$ using a random oligonucleotide priming kit ($^{T7}$QuickPrime™ Kit, Pharmacia Biotech, Uppsala, Sweden) to a specific activity of $1\times10^9$ cpm/$\mu$g DNA excepted for $\alpha$- and $\beta$-MHC using polynucleotide kinase T4 with $\gamma[^{32}P]dATP$. Hybridization was carried out at 420° C.

The amount of labeled mRNA was quantified by scanning laser densitometry (Phosphorimager, Molecular Dynamics; Sunnyvale, USA). Variations in RNA loading and membrane transfer were corrected by densitometric quantification of a negative photograph of 28S and 18S ribosomal RNA bands from ethidium bromide stained RNA gels. Gels with more than 10% variation were redone.

The final values were obtained by using the groups treated by 0.5 and 1.5 nmol T4/day/100 g body weight (depending on the tissue) as control and expressed in arbitrary units. Each membrane contained a 0.5 and/or a 1.5 nmol T4/day/100 g body weight sample. For the RNA levels of pituitary monodeiodinase type 2 the densitometric value of the highest dose of T4 was used as internal standard.

Statistical methods. A Two-way Analysis of Variance (ANOVA) was used to estimate differences among the two treatment groups, over the increasing doses of the hormones (4 levels), and the interaction between treatment and dose levels (SAS General Linear Models program). The dose levels at a 1:3 molar ratio were considered for 1, 3, 9 and 27 times the lowest dose. A one-way analysis of covariance, with Ln (TSH) as the covariate, was performed using BMDP software (1V), which also includes a test for parallel regression slopes. When the two treatment groups shared a common slope, adjusted Heart values for each treatment group were calculated at the overall mean Ln (TSH) concentration. Most variables were log transformed to improve linearity for these analyses. Significance was considered as $p<0.05$.

Results.

Rats treated with Tetrac and T4 gain weight during the 13 days of treatment (see Table 1). With the highest doses of Tetrac and T4 the final weight gain was inferior to the other groups. For both treatments, the increase in liver weight was parallel to the increase in body weight. However, the heart weight increased faster than body weight with increasing infusion rates of T4 while Tetrac was less efficient ($p<0.01$).

TABLE 1

Hypothyroid rats treated for 2 weeks with continuous infusions of Tetrac or T4 (alzet minipumps). Results of heart weights and whole body weights (BW) are shown.

|  | nmol/day/ 100 g BW | | Heart (g) | Heart/ BW (%) |
| --- | --- | --- | --- | --- |
| Tetrac | 1.5 | (0) | 0.76 ± 0.02 | 0.31 ± 0.01 |
| Infusion | 4.5 | (3x) | 0.83 ± 0.04 | 0.33 ± 0.02 |
|  | 13.5 | (9x) | 0.94 ± 0.03 | 0.36 ± 0.01 |
|  | 40.5 | (27x) | 0.98 ± 0.06 | 0.39 ± 0.02 |
| T4 infusion | 0.5 | (0) | 0.86 ± 0.06 | 0.35 ± 0.02 |
|  | 1.5 | (3x) | 0.90 ± 0.04 | 0.34 ± 0.01 |
|  | 4.5 | (9x) | 1.19 ± 0.03 | 0.45 ± 0.02 |
|  | 13.5 | (27x) | 1.32 ± 0.11 | 0.54 ± 0.02 |
| Euthyroid (WM) |  |  | 1.04 ± 0.05 | 0.38 ± 0.01 |
| Hypothyroid |  |  | 0.61 ± 0.03 | 0.27 ± 0.01 | mean ± SEM

Serum Tetrac levels were high but serum Triac levels remained low. The ratio of serum Triac to Tetrac was lower than the T3 to T4 ratio (see Table 2). Despite these high serum Tetrac levels, the contamination of the homogenates with Tetrac was not sufficient to affect the enzyme assay. In brain cortex homogenates the concentration was less than 1 fmol/$\mu$g protein. Addition of Tetrac to a monodeiodinase type 2 assay using microsomol protein from brain cortex showed, with 1 fmol Tetrac/$\mu$g protein, 90.5% of the full activity. Similar results were obtained by addition of T4 or rT3.

TABLE 2

Serum values of TSH, T4, T3, Triac and Tetrac.

|  | nmol/day/ 100 g BW | | TSH (ng/ml) | T3 (pmol/ml) | T4 (pmol/ml) | Triac (pmol/ml) | Tetrac (pmol/ml) |
|---|---|---|---|---|---|---|---|
| Tetrac | 1.5 | (0) | 90.3 ± 8.6* | | | 1.1 ± 0.3 | 168 ± 16 |
| Infusion | 4.5 | (3x) | 4.6 ± 0.5 | | | 1.1 ± 0.2 | 332 ± 19 |
| | 13.5 | (9x) | 1.2 ± 0.3 | | | 2.4 ± 0.5 | 458 ± 27 |
| | 40.5 | (27x) | <0.8 | | | 6.3 ± 1.7 | 406 ± 57 |
| T4 | 0.5 | (0) | 110.2 ± 10.8 | 0.7 ± 2.8 | 43.1 ± 2.8 | | |
| infusion | 1.5 | (3x) | 11.8 ± 3.0 | 1.2 ± 0.1 | 77.1 ± 9.4 | | |
| | 4.5 | (9x) | 1.0 ± 0.2 | 3.4 ± 0.2 | 129.7 ± 9.5 | | |
| | 13.5 | (27x) | <0.8 | 24.0 ± 0.7 | 353.4 ± 31.7 | | |
| Euthyroid (WM) | | | 7.9 ± 1.1 | 2.1 ± 0.2 | 81.9 ± 6.1 | | |
| Hypothyroid | | | 76.7 ± 6.4 | 0.2 ± 0.0 | | | | mean ± SEM Serum TSH values were significantly lower in the Tetrac treated rats when compared to the T4 treated rats with the same molar ratio infusion rate.

Figure 2A:
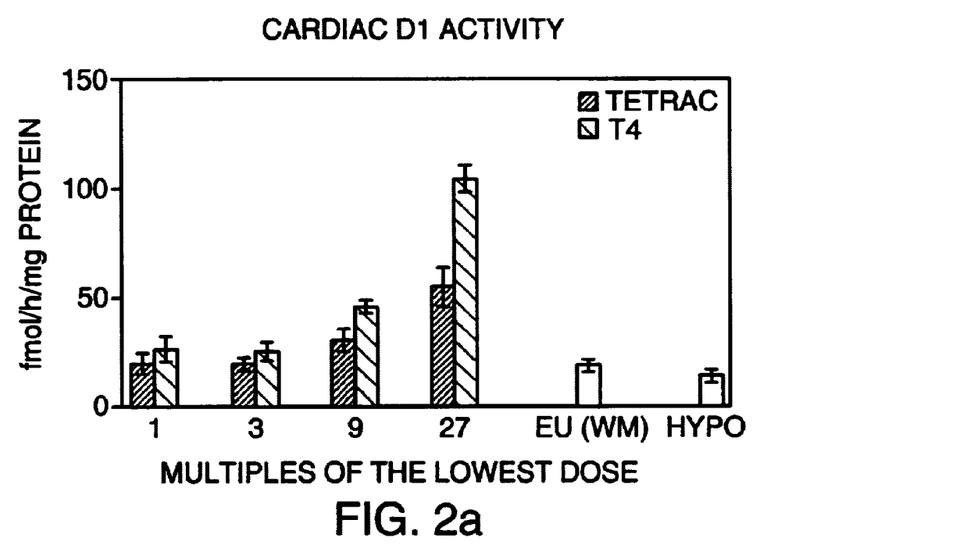
Figure 2B:
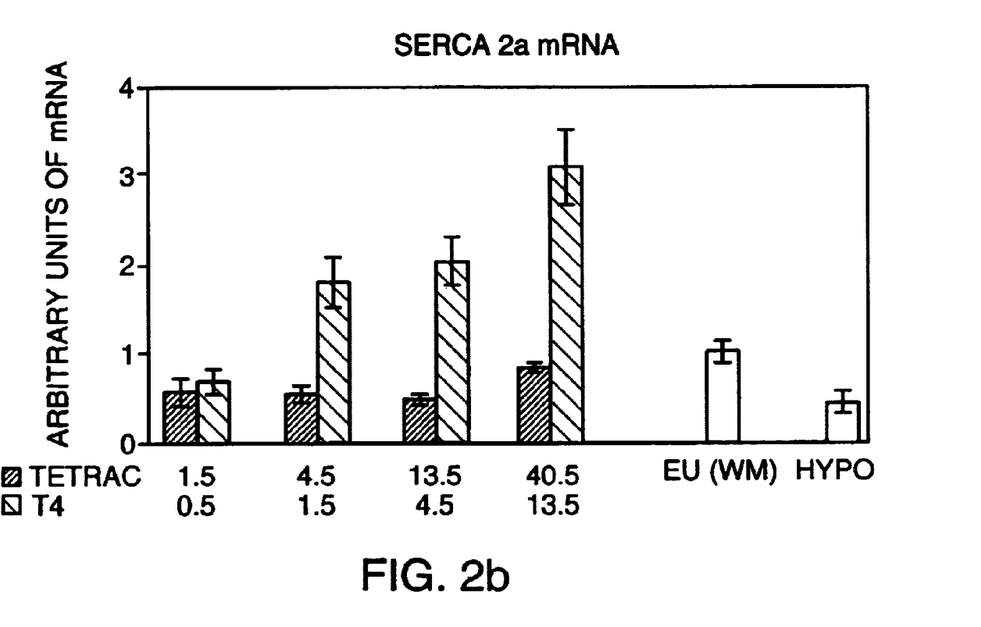
Figure 3A:
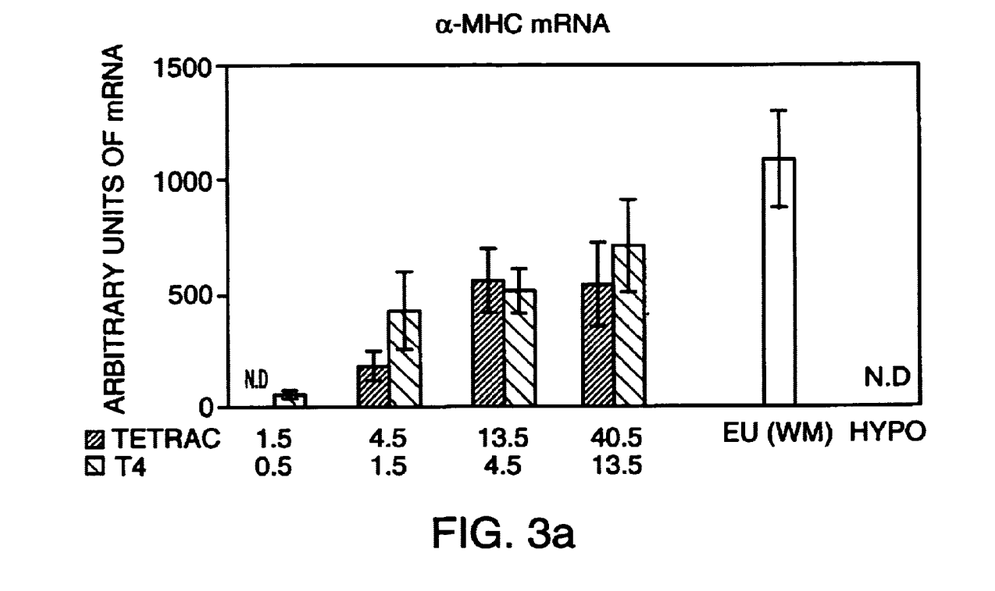
Figure 3B:
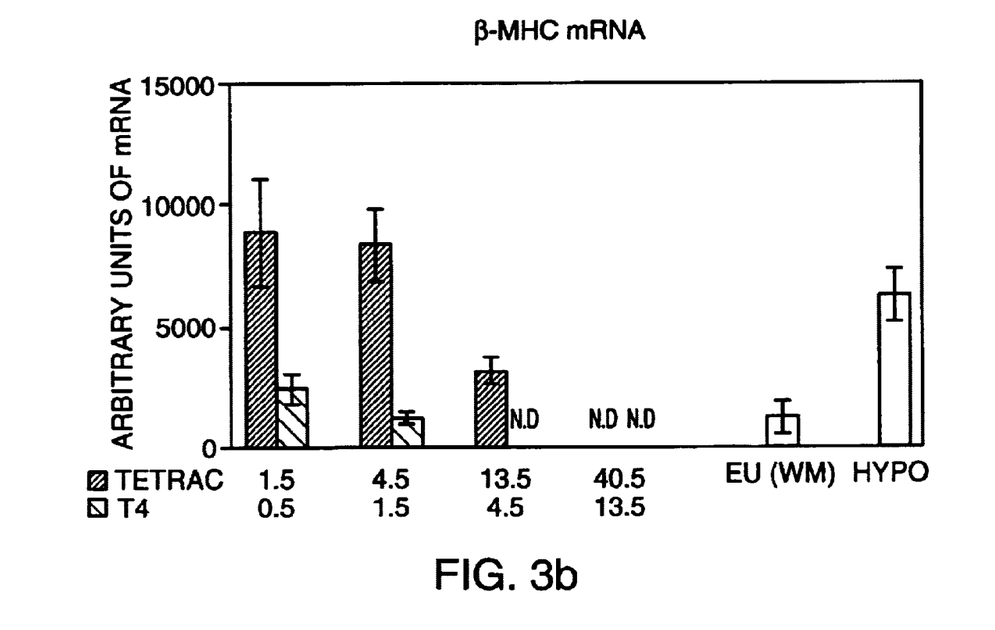

Infusions at a molar T4 to Tetrac ratio of 1 to 3 were used. For this reason, in the analysis of variance (ANOVA) calculations, the molar ratios were used. In FIGS. 2a and b the effects of the 2 hormones on the two cardiac parameters, monodeiodinase type 1 activity and SERCA 2a mRNA levels are shown. Inspection of the two figures demonstrates the weak response to increasing doses of Tetrac compared to T4 (p<0.00 1). In the ANOVA, a significant interaction between the two hormone treatments (p=0.003 for heart monodeiodinase type 1, p=<0.001 for SERCA 2a) verifies this difference in response. For α- and β-MHC there was no interaction with dose and treatment (FIG. 3).

Figure 4A:
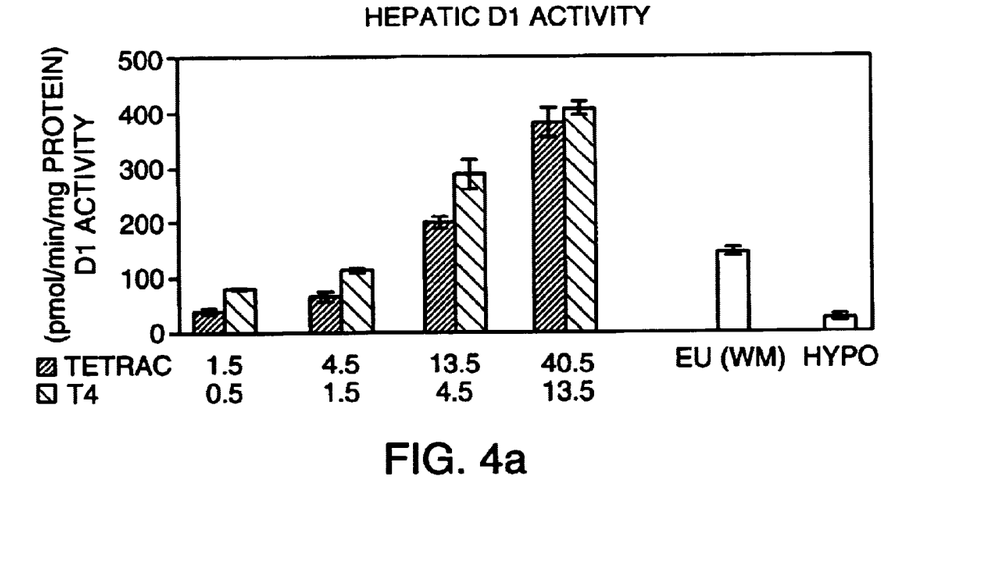
Figure 4B:
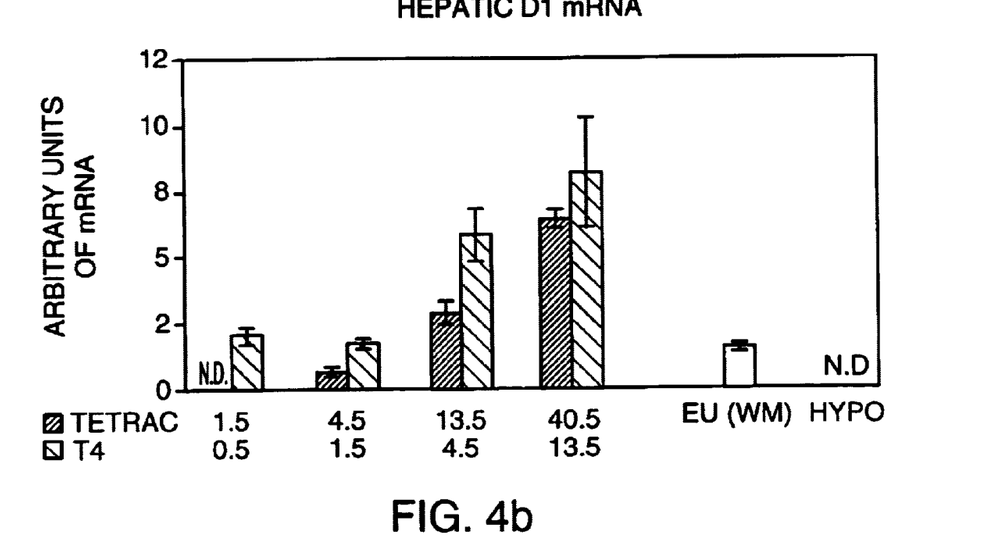
Figure 5A:
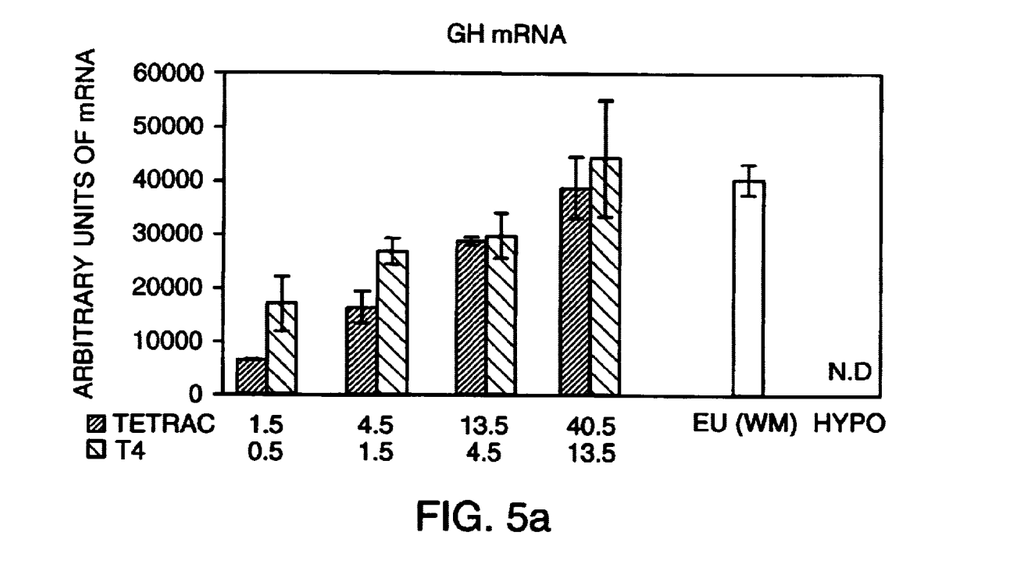
Figure 5B:
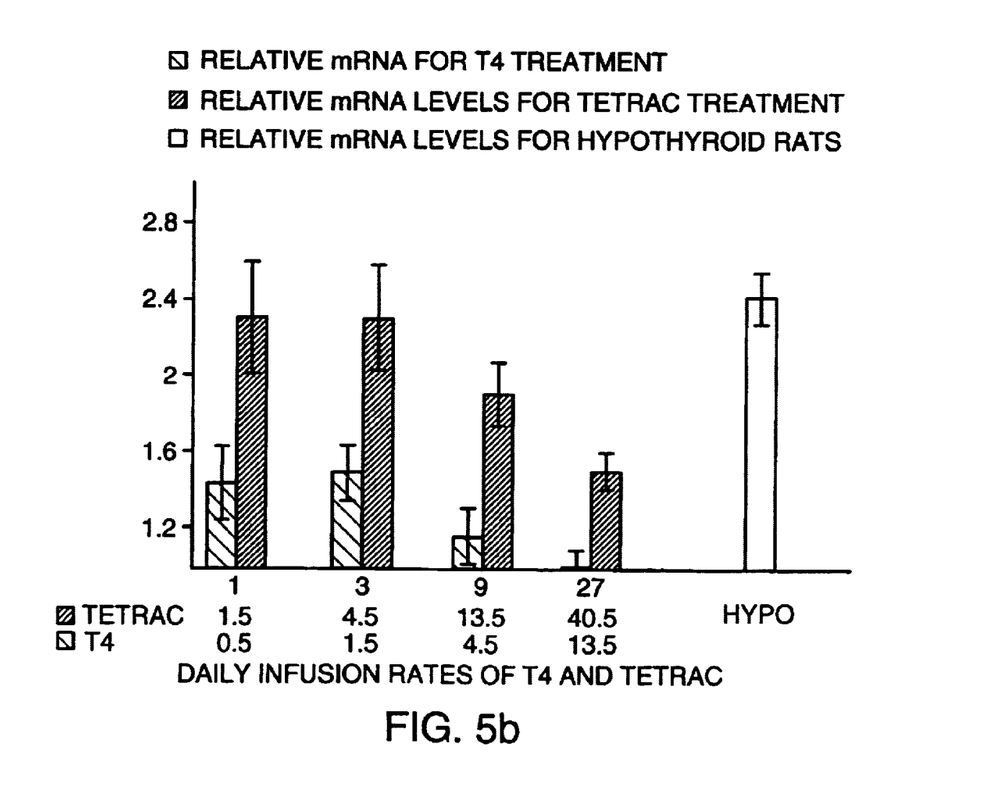

The responses of monodeiodinase type I activity and SERCA 2a mRNA levels contrast with the responses of hepatic monodeiodinase type 1 activity and mRNA, shown in FIG. 4. Here the tissue responses to increasing doses of the two hormones were parallel, and for liver monodeiodinase type 1, the concentrations were significantly higher for the T4 treated rats at all dose levels (p=0.001 and for liver mRNA p=0.053). There was no treatment difference for the response of growth hormone (GH) mRNA (FIG. 5a). However, the inhibition of the mRNA levels of monodeiodinase type 2 was clearly less efficient with Tetrac than with T4, p=0.00 1 (FIG. 5b).

Figure 6A:
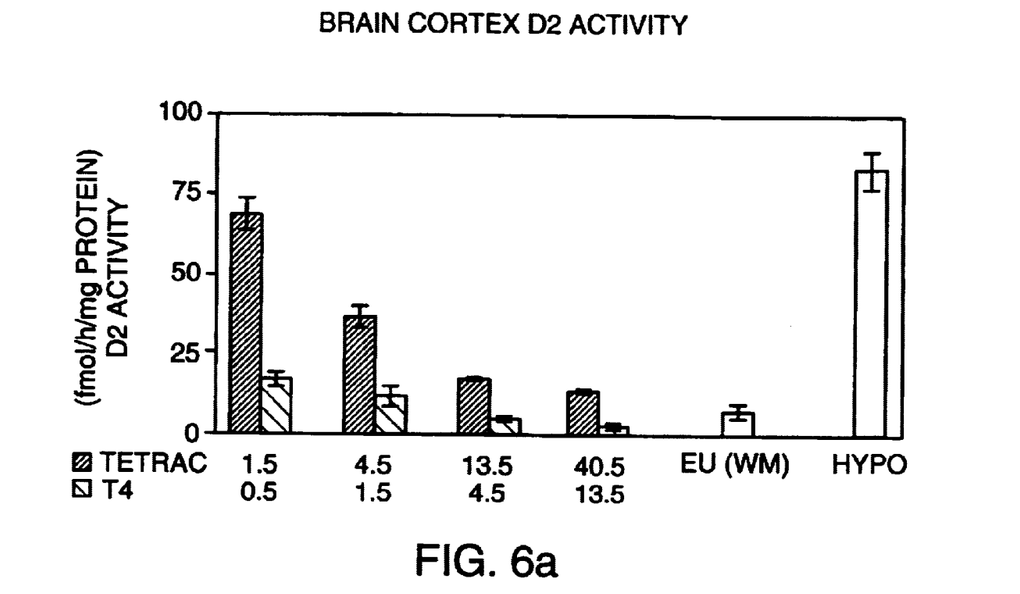
Figure 6B:
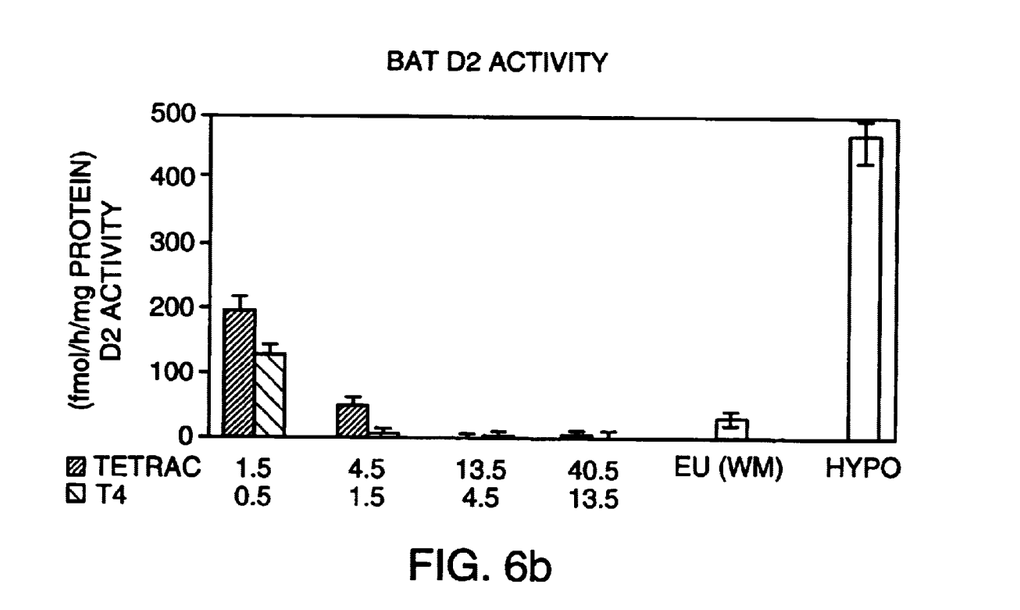
Figure 7:
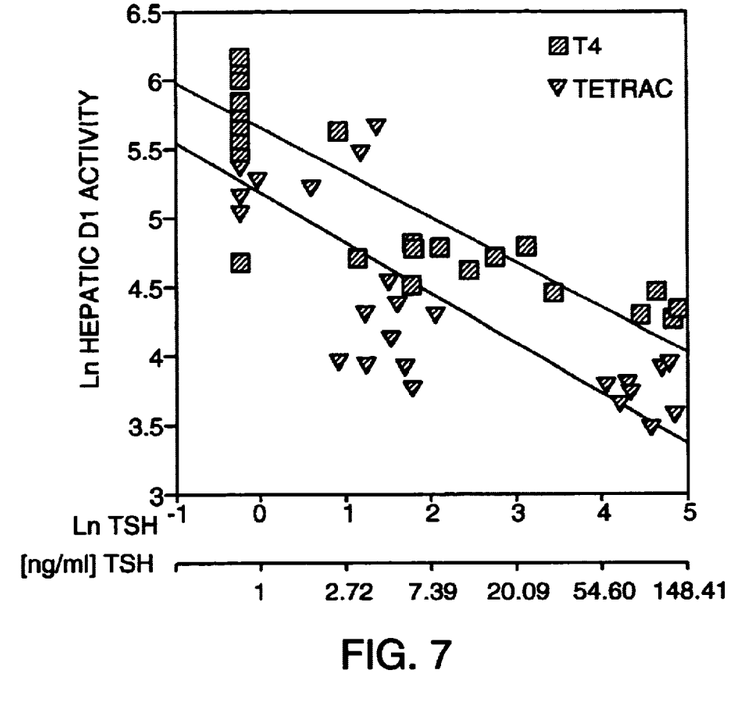
FIG. 7 shows the plot of Ln (TSH) (ng/ml) against Ln (hepatic monodeiodinase type 1 activity).

In FIGS. 6a and b the response of monodeiodinase type 2 activity is illustrated. In brain cortex the effect of Tetrac is clearly less than that of T4 (p=0.001) and in brown adipose tissue the difference is also present (p<0.001) but less striking. A significant interaction between treatment and the changing doses was p=0.001 for brain and p<0.01 for BAT. Serum TSH concentrations were found to be higher in the T4 treated rats compared to the Tetrac treated rats (mean of 31 vs. 24 ng/ml, p=<0.04). Thus, the data was subjected to an analysis of covariance with the natural log of TSH (Ln (TSH)) as the covariate. For those variables where the two treatment groups had a similar response slope compared to their Ln (TSH) concentrations, adjusted group means could be calculated at the overall group Ln (TSH) concentration. FIG. 7 demonstrates the plot of Ln (TSH) against Ln (hepatic monodeiodinase type 1 activity). The results are summarized in Table 3. They indicate that at an equal serum TSH concentration, hepatic monodeiodinase type 1 activity and mRNA levels are less stimulated in Tetrac treated rats (59 and 49% of the value in T4 treated rats). Tetrac was also less active than T4 in reducing the excessive monodeiodinase type 2 activity characteristic for hypothyroid cortex and brown adipose tissues. In Table 3 the results are expressed in terms of remaining activity and therefore, the activity of the enzyme was higher with the poorer inhibitor.

TABLE 3

Levels of hepatic monodeiodinase type I and 2 activities and the levels of mRNA of hepatic monodeiodinase type 1, MHC and growth hormone (GH) in tetrac and T4 infused rats.

| | | | Adjusted Means* | | | | |
|---|---|---|---|---|---|---|---|
| Measurement | Organ | N | Tetrac infused rats | T4 infused rats | T4/Tetrac** | Tetrac/T4 | p Value |
| Residual Monodeiodinase type 1 activity | Liver | 62 | 106 | 180 | | 59% | <0.001 |
| Residual Monodeiodinase type 1 mRNA | Liver | 27 | 2.48 | 5.1 | | 49% | <0.03 |
| Residual monodeiodinase type 2 activity | Brain Cortex | 61 | 27.7 | 5.02 | 18% | | <0.001 |
| Residual monodeiodinase type 2 activity | BAT | 61 | 28 | 11.8 | 42% | | <0.001 |

TABLE 3-continued

Levels of hepatic monodeiodinase type I and 2 activities and the levels of mRNA of hepatic monodeiodinase type 1, MHC and growth hormone (GH) in tetrac and T4 infused rats.

| | | | Adjusted Means* | | | | |
|---|---|---|---|---|---|---|---|
| Measurement | Organ | N | Tetrac infused rats | T4 infused rats | T4/Tetrac** | Tetrac/T4 | p Value |
| α-MHC mRNA | Heart | 20 | 5.3 | 1.13 | 21% | | <0.001 |
| β-MHC mRNA | Heart | 24 | 328 | 495 | | 66% | 0.19 |
| GH mRNA | Pituitary | 30 | 20280 | 28644 | | 71% | 0.07 |

The adjusted group means for each variable were estimated by analysis of covariance at the mean Ln (TSH) concentration. For SERCA 2a and cardiac monodeiodinase type 1 the slopes between T4 and Tetrac treatment were different and therefor the mean potency could not be estimated. The mRNA levels are expressed in arbitrary units (Phosphorimager).
*for each measurement in T4 and tetrac treated rats
**Activity of T4 in % of Tetrac; Activity of Tetrac in % of T4
GH: growth hormone
BAT: brown adipose tissue

EXAMPLE 3

Evaluation of the Toxicity of Tetrac in Cynomologus Monkeys

Preparation of Tetrac for injection. Tetrac from Rhône-Poulenc and Henning Laboratory were compared. Tetrac powder was dissolved in sterile 0.1 N NaOH at 2 mg/ml. This solution was made before the beginning of each treatment period and stored at 4° C. in polypropylene tubes, protected from light. Each solution for injection was prepared daily after dilution in the vehicle (0.9% NaCl) containing 5% monkey serum (v/v), and was stored at room temperature and protected from light, according to the storage conditions of the test substance.

Animals. One male and one female purpose bred Cynomologus monkeys Macaca fascicularis were supplied by Centre de Recherches Primatologiques, Port Louis, Mauritius. The animals were approximately six years old and had a body weight of 5.8 kg for the male and 6.2 kg for the female. The animals were individually housed in stainless steel cages and a metallic tray was placed under each cage in order to collect urine. The animals were fed daily with approximately 200 grams each of U.A.R. 107 C pelleted diet (batch Nos. 61106, 61207 and 70317, U.A.R., Villemoisson-sur-Orge, France), distributed about 2 hours after treatment with Tetrac. No contaminants were known to have been present in the diet, drinking water or bedding material at levels which may be expected to have interfered with or prejudiced the outcome of the study.

Treatment with Tetrac. Details of the treatment and dose-level are given in Table 4.

TABLE 4

Treatment regime for Cynomologus monkeys (1 male and 1 female) over a 12 week period.

| Week of Treatment | TETRAC supplier | Animal | Dose-level (μg/kg/day) |
|---|---|---|---|
| 1 to 3 | Rhône-Poulenc | male | 75 |
| | Henning | female | |
| 4 to 6 | — | male | — |
| | | female | |
| 7 to 9 | Henning | male | 75 |
| | Rhône-Poulenc | female | |
| 10 to 12 | — | male | — |
| | | female | |

Weeks 1 to 3 and weeks 7 to 9: the animals received the test substance TETRAC provided either by Rhone-Poulenc or by Henning Laboratories over a three-week period.

Weeks 4 to 6 and weeks 10 to 12: a washout period of three weeks was observed.

Administration of Tetrac. Tetrac was administered via intramuscular injection into the thigh muscle once a day, at approximately the same time each day, several days a week over a three week period. The quantity of tetrac administered to each animal was adjusted according to the most recently recorded body weight. A constant dosage-volume of 0.5 ml/kg was used.

Clinical Examinations of the Monkeys.

Morbidity and mortality. The animals were checked at least twice a day, for mortality and signs of morbidity.

Clinical signs. The animals were observed at least once a day, at the same approximate time each day.

Body weight. Body weight was recorded for each animal once before the beginning of the treatment period, on the first day of the treatment period, and at least once a week until the end of the study.

Food consumption. Food consumption was estimated for each animal by calculating the difference between the quantity given and that remaining the next morning. This was estimated daily during the week before treatment and throughout the study. Food consumption was expressed as a percentage of the quantity given. Whenever fasting was required, the food was removed at the end of the day and the estimation of consumption was made at that time, food being made available for approximately five hours on that day.

Results.

Mortality. No deaths occurred during the study.

Clinical signs. No clinical signs were observed during the treatment of washout periods.

Body weight. The body weight gains recorded over the treatment or washout periods are presented in Table 5.

TABLE 5

Body weight gains of the Cynomologus monkeys over the course of the 12 week treatment with Tetrac.

| | Body Weight | |
|---|---|---|
| | Tetrac from Rhône-Poulenc | Tetrac from Henning Laboratory |
| Male | | |
| treatment period | +100 g (+2%) | +200 g (+3%) |
| washout period | +100 g (+2%) | 0 |
| Female | | |
| treatment period | +300 g (+8%) | +300 g (+9%) |
| washout period | 0 | +100 g (+3%) |

A slightly higher body weight gain was recorded in the female over the two treatment periods when compared to the washout periods without relevant differences between the two tetrac suppliers. No relevant differences were noted in the male between the treatment or washout periods.

Food Consumption. The estimated food consumption was 75% or 100%, expressed in days of observation/number of days in concerned period, as shown in Table 6.

TABLE 6

Food consumption for the Cynomologus monkeys over the course of the 12 week treatment period with Tetrac.

| | Food Consumption | | | |
|---|---|---|---|---|
| | Tetrac from Rhône-Poulenc | | Tetrac from Henning Laboratory | |
| Male | | | | |
| pretreatment | 100%: 7/7 | — | | |
| treatment period | 100%: 20/21 | 75%: 1/21 | 100%: 21/21 | |
| washout period | 100%: 21/21 | | 100%: 21/21 | |
| Female | | | | |
| pretreatment | — | | 100%: 6/7 | 75%: 1/7 |
| treatment period | 100%: 14/21 | 75%: 7/21 | 100%: 8/21 | 75%: 13/21 |
| washout period | 100%: 16/21 | 75%: 5/21 | 100%: 18/21 | 75%: 3/21 |

A tendency for slightly lower food consumption by the female was recorded over the treatment period with tetrac provided by Henning Laboratory. In the male, the food consumption was unaffected by the treatment.

EXAMPLE 4

Suppression of TSH by Tetrac as Compared to T4 in Humans

A patient receiving 200 µg/day dose of T4 was withdrawn from T4 treatment and treated with Tetrac for 21 days with a dose of 2100 µg/day. The results can be seen in FIG. 8.

Figure 8:
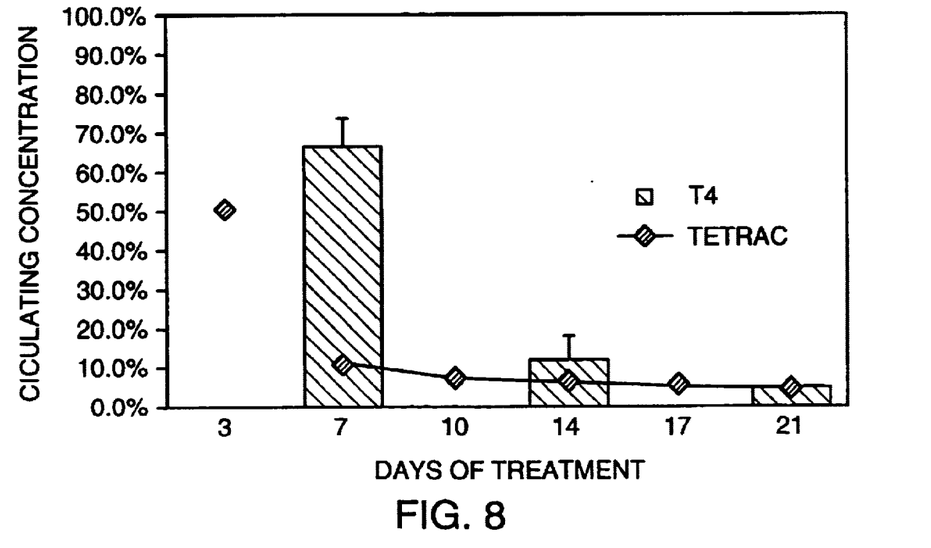
FIG. 8 shows the circulating levels of TSH in human patients withdrawn from T4 treatment and then subsequently treated with a daily dose of either tetrac or T4 for 21 days.

TSH was rapidly suppressed from 151.0 mU/L to 6.3 mU/L over the 21 days of treatment. Circulating concentration depicts the percent suppression of TSH from the markedly elevated levels following T4 withdrawal This is compared to 6 patients treated conventionally with 200 µg T4/day following the initial withdrawal of T4.

The invention has been described in detail with reference to preferred embodiments thereof. However, it will be appreciated that those skilled in the art, upon consideration of this disclosure, may make modifications and improvements within the spirit and scope of the invention as set forth in the following claims.

What is claimed is:

1. A method for suppressing TSH secretion while reducing or avoiding the thyromimetic stimulation of peripheral tissues induced by a dose of L-thyroxine which produces an equivalent TSH-suppressive effect comprising administration of a pharmaceutical composition comprising tetrac, or a pharmaceutically acceptable salt thereof, admixed with a pharmaceutically acceptable carrier.

2. The method of claim 1 for treatment of a patient suffering from malignancy or other abnormal growth of the thyroid.

3. The method of claim 1 for treatment of a patient suffering from hypothyroidism.

4. A method for suppressing TSH secretion while reducing or avoiding the thyromimetic stimulation of the tissues of the heart, liver, kidneys, muscle or bone as compared to the stimulation of said tissues induced by a dose of L-thyroxine which produces an equivalent TSH-suppressive effect, comprising administration of a pharmaceutical composition comprising tetrac, or a pharmaceutically acceptable salt thereof, admixed with a pharmaceutically acceptable carrier.

5. A method for suppressing TSH secretion while reducing or avoiding the thyromimetic stimulation of the tissues of the heart as compared to the stimulation of said tissues induced by a dose of L-thyroxine which produces an equivalent TSH-suppressive effect, comprising administration of a pharmaceutical composition comprising tetrac, or a pharmaceutically acceptable salt thereof, admixed with a pharmaceutically acceptable carrier.

6. A method for long-term treatment of patients with malignancies or abnormal growths of the thyroid gland, comprising administration of a pharmaceutical composition comprising tetrac, or a pharmaceutically acceptable salt thereof, admixed with a pharmaceutically acceptable carrier.

7. A method for suppressing growth of residual thyroid tissue in a patient post thyroidectomy comprising administration of a pharmaceutical composition comprising tetrac, or a pharmaceutically acceptable salt thereof, admixed with a pharmaceutically acceptable carrier.

* * * * *

UNITED STATES PATENT AND TRADEMARK OFFICE
CERTIFICATE OF CORRECTION

PATENT NO. : 6,740,680 B1
DATED : May 25, 2004
INVENTOR(S) : Danforth, Jr. et al.

It is certified that error appears in the above-identified patent and that said Letters Patent is hereby corrected as shown below:

Title page,
Item [54], Title, "PHARMACEUTICAL COMPOSITIONS TO TETRAC AND METHODS OF USE THEREOF" should be changed to -- PHARMACEUTICAL COMPOSITIONS OF TETRAC AND METHODS OF USE THEREOF --
Item [73], Assignee, "Becton Pharma, Inc." should be changed to
-- BEARTOWNPHARMA, INC. --

Column 1,
Line 52, "therefor" should be changed to -- therefore --

Column 3,
Line 47, "SERCA" should be changed to -- SECRA 2a --
Lines 65-66, "in human patients" should be changed to -- in a human patient --

Column 4,
Line 42, "fluol" should be changed to -- fmol --

Signed and Sealed this

Second Day of November, 2004

JON W. DUDAS
*Director of the United States Patent and Trademark Office*